United States Patent [19]

Yamada

[11] Patent Number: 4,479,291

[45] Date of Patent: Oct. 30, 1984

[54] HAIR IMPLANTING APPLIANCE

[75] Inventor: Shiro Yamada, Aichi, Japan

[73] Assignee: Nido, Ltd., Tokyo, Japan

[21] Appl. No.: 415,849

[22] Filed: Sep. 8, 1982

Related U.S. Application Data

[63] Continuation-in-part of Ser. No. 165,241, Jul. 2, 1980, Pat. No. 4,378,019.

[30] Foreign Application Priority Data

Jul. 3, 1979 [JP] Japan ............................. 54-83509

[51] Int. Cl.$^3$ ............................................. A61B 17/00
[52] U.S. Cl. ................................................... 128/330
[58] Field of Search .................... 128/330, 339, 329 R; 46/172; 132/53, 56; 112/48, 169; 223/102, 104

[56] References Cited

U.S. PATENT DOCUMENTS

| 3,513,860 | 5/1970 | Kost | 132/56 X |
| 4,216,777 | 8/1980 | Pridemore | 128/330 |
| 4,221,212 | 9/1980 | Miller | 128/330 X |

FOREIGN PATENT DOCUMENTS

| 1953026 | 2/1972 | Fed. Rep. of Germany | 128/330 |
| 2843072 | 4/1979 | Fed. Rep. of Germany | 128/330 |
| 765220 | 1/1957 | United Kingdom | 128/329 R |

Primary Examiner—Michael H. Thaler
Attorney, Agent, or Firm—Browdy and Neimark

[57] ABSTRACT

A hair implanting appliance for directly implanting an artificial hair in a human skin comprises a needle formed at its leading end with a notch which is sized and shaped to retain the root portion of the hair. The needle is snugly and slidably received in the through hole of a sheath such that its leading end can protrude from the leading end of the sheath into the human skin to a depth necessary for the hair implantation. The sheath has at least a portion of its leading open end merge into the open edge of the notch at the leading end of the needle when this needle is retracted into the sheath and this structure forms the guide surface of the root portion retained in the notch.

12 Claims, 20 Drawing Figures

HAIR IMPLANTING APPLIANCE

This is a continuation-in-part of parent, copending application Ser. No. 165,241 filed July 2, 1980, now U.S. Pat. No. 4,378,019, the contents of which are incorporated herein by reference.

FIELD OF THE INVENTION

The present invention relates to improvements in a hair implanting appliance for directly implanting artificial hairs into human skin.

BACKGROUND OF THE INVENTION

The technique for directly implanting artificial hairs in human skin has been remarkably developed in recent years, and various types of artificial hairs and their implanting appliances have accordingly been improved in a number of forms. As to the shapes of the root portions of the hairs, for instance, various proposals have been made including providing an ampoule shape (U.S. Pat. No. 4,024,315), an arrowhead shape (Japanese Patent Publication No. 54-11744), a looped shape and a knot which is formed at the root portion.

As to hair implanting appliances, on the other hand, various developments have been made including a hollow needle (U.S. Pat. No. 4,004,592), an air gun type hair implanter (Japanese Patent Publication No. 54-11744), a hair implanting needle formed with a recess at its tip (U.S. Pat. No. 4,004,592), a pincette-shaped hair implanting needle (U.S. Pat. No. 4,004,592) and a bifurcated needle (U.S. Pat. No. 4,004,592).

The most slender hair implanting needle according to the prior art has an outside limit diameter of 0.3 mm for the case of a hollow structure and a limit diameter of 0.35 to 0.5 mm for the case of a bifurcated or similar structure. This is because it becomes difficult to insert any artificial hair into the hollow needle which has a smaller outside diameter than the above-specified value. In the case of a bifurcated needle, having a smaller diameter than the above-specified value, it may bend when the needle is pierced into the skin, so that it cannot carry out its function. If, moreover, the thickness of the needle is excessively reduced, the retaining operation of the artificial hair at the tip of the bifurcated needle becomes so deficient as to cause the hair implanting operations to be deteriorated.

In order to enhance the fixation percentage of the artificial hairs implanted, emphasis has been placed upon the shape of the hair root portion for increasing its resistance to extraction and upon research for the developments of needles which are best suited for implanting the artificial hairs.

SUMMARY OF THE INVENTION

Although the shape of the hair root portion plays an important role in enhancing the fixation percentage of the hairs, it has now been discovered that the fixation percentage is more dependent upon the extent of breakage of the epidermis and hypodermal tissue of the human skin. More specifically, if the epidermis and the hypodermal tissue are heavily broken when they receive the artificial hair, it takes much time for the wound to be restored so that the implanted root portion may be removed by external force before it is sufficiently fixed, with the resultant deterioration in the fixation percentage immediately after the hair implantation. Moreover, if this instable or unfixed term is long, inflammation or suppuration is liable to take place causing further reduction in the hair fixation percentage.

With this in mind, it is therefore necessary to minimize the thickness of the hair implanting needle and to devise both the shape of the hair root portion which can minimize the wound when the hair is implanted and the shape of the hair implanting needle which can be used in combination with that root portion. Yet this must be done without violation of the reasons prior implanting needles have not been made smaller, as noted above.

It is, accordingly, an object of the invention to overcome deficiencies in the prior art, such as indicated above; a further object is to provide for improved implantation of artificial hair.

It is another object of the present invention to provide a hair implanting appliance which can maintain the strength necessary for the hair implantation and can facilitate the retaining operation of an artificial hair at the tip of a needle even if the thickness of the needle is reduced.

According to a major aspect of the present invention, there is provided a hair implanting appliance comprising: means to penetrate the scalp comprising a needle having its leading end formed with a notch which is sized and shaped to retain the root portion of an artificial hair to be implanted; and means to guide the needle without penetrating the scalp comprising a sheath formed with a through hole which has substantially the same inside diameter as the outside diameter of said needle, the needle being slidably received in the sheath such that the leading end of the needle can be extended from the leading end of the sheath which abuts the scalp into a human skin to a depth necessary for the hair implantation and such that the sheath has at least a portion of its leading open end, which is to merge into the open edge of the notch at the leading end of the needle when the needle is retracted into the sheath, forming the guide surface of the root portion to be retained. Such guide surface portion of the leading end of the sheath cooperates with the notch in the leading end of the needle to better control the positioning of the hair root in the appliance.

The most satisfactory artificial hair that can be implanted by the appliance according to the present invention is prepared such that its leading end is curled to form a looped root portion. Artificial hairs having other shapes can also be used if their necks leading to the root portions can be retained by the leading end notch of the needle.

On the other hand, the needle to be used in the hair implanting appliance according to the present invention may be formed with a U-shaped notch at the side wall of the leading end thereof.

Moreover, a sheath which has its leading open end obliquely cut can be used in a similar manner. In this case, one side of the U-shaped notch of the needle merges into the open end of the sheath thereby to form a guide surface in which the root portion is retained. The other side of the notch of the needle protrudes beyond the sheath to easily receive the root portion and retain it in the notch.

The sheathes thus far described can also be used in the case of the needle which is formed along its side wall with a U-shaped notch. In addition, there can be used a sheath which has its leading end so cut only at the semicircumference that the open end of the cut merges into the lower edge of the open portion of the U-shaped notch. In case a sheath of this type is used, the remaining semicircumference of the sheath partly protects the tip of the hair implanting needle and partly further facilitates the retaining operation of the looped root portion in the needle tip.

Instead one desirable shape of the U-shaped notch of the hair implanting needle is made such that its inlet is wide enough to receive the root portion of the hair to be retained without any difficulty and that it becomes increasingly narrowed. However, the shape of the notch may be freely modified from the machining requirements such that it has the same width at the inlet and at the bottom and such that the bottom is angled or rounded if the modification is within such a range as to raise no obstacle to the reception of the root portion of the hair.

In the hair implanting appliance according to the present invention, the needle is slidably received in the sheath. A dolly member formed with a bulged portion having an enlarged diameter is fixed to the base portion of the needle. A spring is mounted between the sheath and the dolly member thereby to urge the needle into the sheath at all times.

At the most retracted position, in which the needle is retracted into the sheath, as has been described above, the leading open end of the sheath forms the guide surface for guiding the artificial hair into the notch, which is formed at the tip of the needle for retaining the hair. It is therefore necessary to make such a construction that the sheath and the needle are prevented from shifting in the circumferential direction relative to each other. While this objective may be accomplished in a variety of ways, according to the simplest method either the needle or the dolly member fixed to the former is cut at its side wall in the longitudinal direction to form either a flat portion or a key way. This flat portion or key way is made coactive with the member, which is disposed to protrude into the through hole of the sheath, so that the needle may slide in the axial direction but not in the circumferential direction.

According to the hair implanting appliance of the present invention having the construction thus far described, since the sheath effectively increases the strength of the hair implanting needle, the diameter of the needle can be reduced to less than two thirds the conventional one, i.e. to only 0.2 to 0.25 mm.

BRIEF DESCRIPTION OF THE DRAWINGS

FIGS. 5 to 10 are partially sectional views showing various modifications of the needle tip and the open end of the sheath, with FIGS. 8-10 showing a preferred embodiment in different positions of use.

DESCRIPTION OF THE PREFERRED EMBODIMENTS

Figure 1:
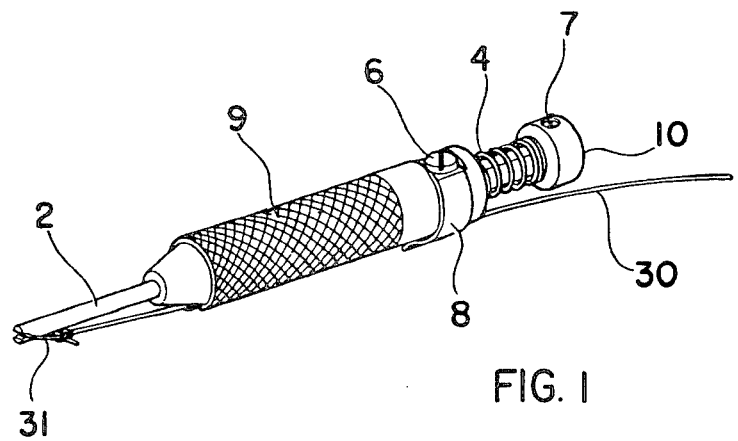
FIG. 1 is a perspective view showing a hair implanting appliance according to the present invention.
Figure 2:
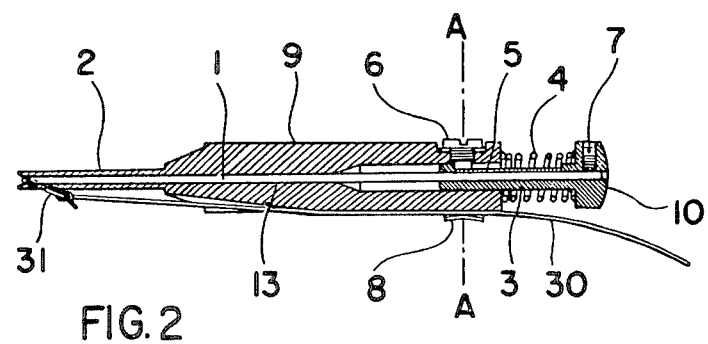
FIG. 2 is a longitudinal section of FIG. 1.

The embodiments of the present invention will now be described with reference to the accompanying drawings.

Referring first to FIGS. 1 to 4, a hair implanting needle 1 is formed at its leading end with a U-shaped notch 11 and is fixed at its base to a dolly member 3 by means of a screw 7. The needle 1 is slidably received in the through hole 13 which is formed in both a sheath 2 and a handle member or grip 9 integral therewith. By the engagement between a key way 5, which is formed in the dolly member 3 fixed to the needle 1, and a screw 6 which is fastened into the grip 9 from the outside and extends into the through-hole 13, the needle 1 is prevented from rotating relative to the sheath 2, and the stroke of the needle 1 between the most protruding position and the most retracted position is preset.

Between the head 10 of the dolly member 3 and the grip 9, there is mounted a coil spring 4 for urging or biasing the needle 1 into the sheath 2 to its most retracted position.

The device is also provided with a retainer element 8 in the form of a leaf spring. The artificial hair 30 thus retained by its root portion 31 in the U-shaped notch 11 and has its body portion gently held on the handle 9 by means of the rounded leaf spring 8.

Figures 3, 4:
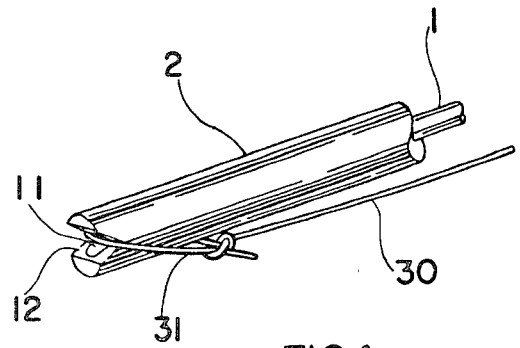
FIG. 3 is a transverse section along line A—A of FIG. 2.
FIG. 4 is an enlarged perspective view showing the tip portion of the needle.
Figure 5:
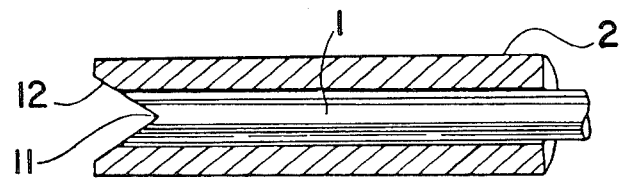

FIG. 5 is a longitudinal section showing the same embodiment as that of FIG. 4 in an enlarged scale, whereas FIGS. 6 to 10 show other embodiments of the hair implanting needle and its sheath. In FIG. 5, it is seen that the notch 12 of the sheath 2 separates the tip of the sheath 2 into two facing semi-circular lips.

Figure 6:
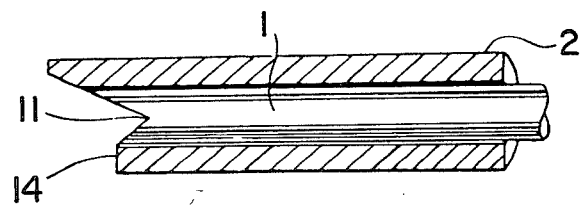

In the embodiment shown in FIG. 6, more specifically, the needle 1 is substantially the same as that of FIG. 5 in that it is formed at its tip with a V-shaped notch 11. However, one of the lips of the tip of the sheath 2 is removed i.e. a portion corresponding to one side of the V-shaped notch, to thereby form semi-circular flat edge 14. This structure enables the looped root portion 31 to be hooked obliquely over the flat portion 14 with more ease compared to the FIG. 5 structure.

Figure 7:
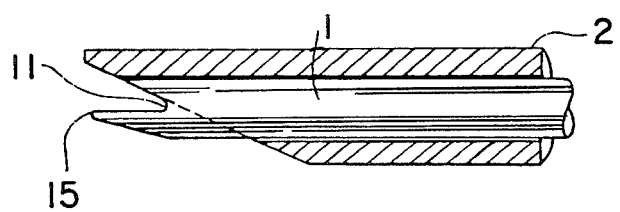

In the embodiment shown in FIG. 7, on the other hand, the tip end of the sheath 2 is obliquely cut. A U-shaped notch 11 of the needle 1 has its one side protruding to form a protrusion 15, on which the looped root portion 31 is hooked and retained. According to this embodiment, the looped root portion 31 is placed over the tip of the needle 1 with the needle 1 slightly protruding beyond the sheath 2. When the needle 1 is then retracted into the sheath 2 to the position shown in FIG. 7, the root portion 31 is guided by the open end of the sheath 2 until it naturally falls into the U-shaped notch 11 where it can be retained.

Figure 8:
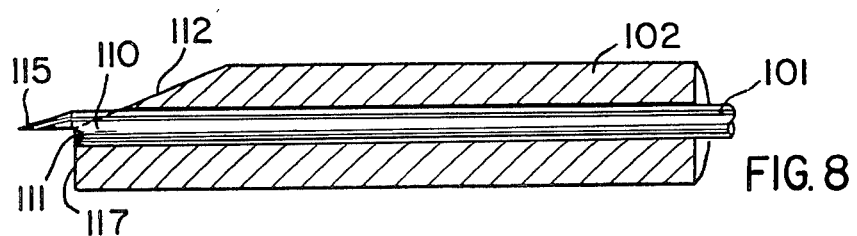
Figures 9A, 9B, 9C, 10:
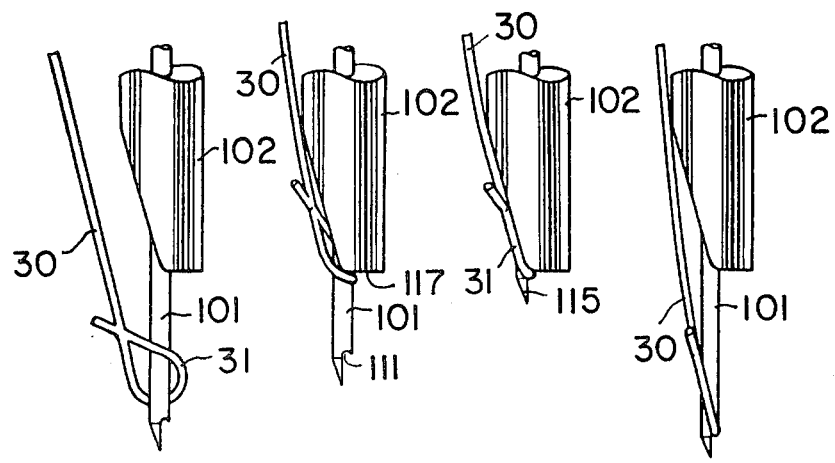

FIGS. 8-10 show another embodiment in which a needle 101 guided in a sheath 102 is provided at its leading end 110 with a protrusion 115 and a U-shaped notch 111 for retaining the root portion of the artificial hair to be implanted. The leading end of the sheath 102 is provided with a blunt, scalp abutting surface 117 essentially disposed at a right angle to the axis of the needle 101 and sheath 102, and is also provide with a diagonal surface 112 obliquely cut at a suitable angle as shown ranging from about 20° to about 60° from the axis of the sheath and needle, such diagonal surface 112 terminating at the leading end of the sheath 102 which passes through at approximmately the axis of said sheath. In a preferred embodiment, the needle 101 has a diameter of approximately 0.23 mm, the U-shaped notch 111 having a maximum width equal to approximately the radius of said needle 101.

The embodiment of FIG. 8 is particularly easy to use as is illustrated in FIGS. 9a-9c and 10, which description applies equally to the use of the embodiment of FIG. 7. Thus, in FIG. 9a, the looped root portion 31 of the artificial hair 30 is passed around the needle 101 as it protrudes from the sheath 102. In FIG. 9b, the artificial hair 30 is pulled upwardly to a slight degree and the needle 101 begins to be retracted into the sheath 102. In FIG. 9c the retraction of the needle 101 has progressed to the point where the lip of the U-shaped notch 111 becomes aligned with the blunt end 117 of the sheath 102, whereupon the root portion of the hair 30 naturally comes to rest in the U-shaped notch 111.

Figures 16, 17, 18:
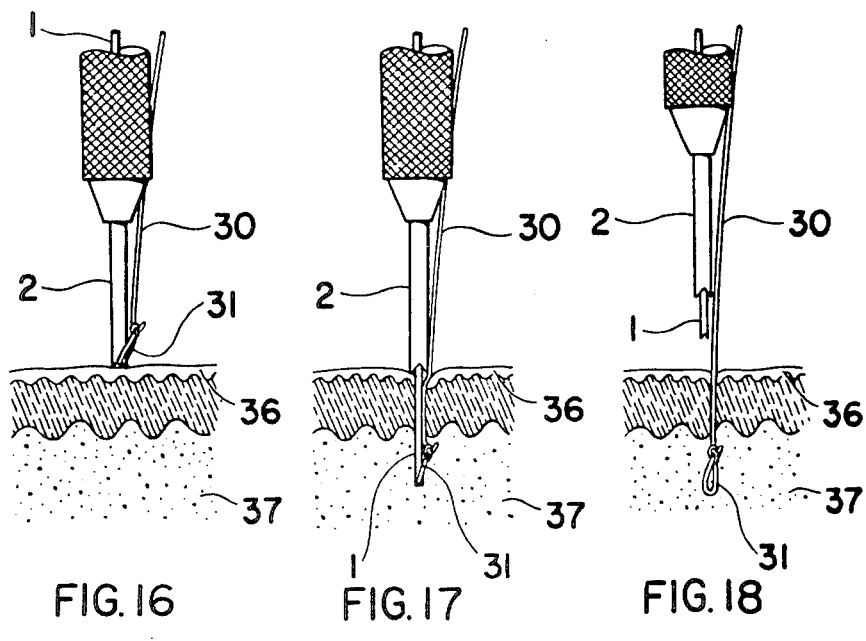
FIGS. 16 to 18 are explanatory views illustrating the using method of the appliance of the present invention.

FIG. 10 shows the artificial hair 30, with its loop 31 retained by the needle 101 in its notch 111, being projected downwardly from the sheath 102 as would be the case if the hair were being implanted in the scalp as also showed in FIGS. 16-18. It will be understood, particularly upon consideration of FIGS. 9b and 9c, that the blunt end 117 of the sheath 102 cooperates with the needle 101 to better control the positioning of the hair root in the appliance.

Figures 11, 12, 13, 14, 15:
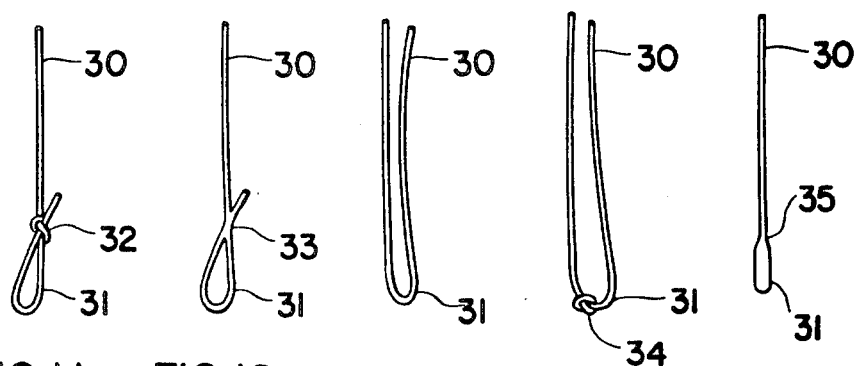
FIGS. 11 to 15 are illustrative views showing various artificial hairs to be used with the appliance of the present invention.

Turning to FIGS. 11 and 12, the preferred artificial hair for the present invention is prepared such that the leading end of the artificial hair 30 is curled to form the looped root portion 31. The example shown in FIG. 11 is formed by knotting the looped root portion 31 as at 32, whereas the preferred example shown in FIG. 12 is formed by welding the root portion 31 as at 33.

FIG. 13 shows another example of the artificial hair 30 in case a long monofilament has its middle portion hooked by the tip of the needle and thrust into the skin so that the bent portion forms the root portion 31.

FIG. 14 is an example which is improved from the example of FIG. 13 such that the bent portion is knotted at 34 to form the root portion 31.

In a further example shown in FIG. 15, the artificial hair 30 is formed at its leading end with the root portion 31 which is bulged into an anpoule shape. If the hair 30 is retaineeed at the neck 35 of its root portion 31 in the V-shaped notch 11 of the hair implanting needle 1 of the present invention, it can be implanted in a similar manner to those of the foregoing examples.

Use of the hair implanting appliance according to the present invention is as follows.

As shown in FIG. 16, the leading end of the sheath 2 is applied to the epidermis 36 of a human skin with the looped root portion 31 of the artificial hair 30 being hooked in the V-shaped notch 11 of the needle tip. When the dolly member 3 fixing the needle 1 is pushed down by the finger of an operator, the needle 1 is thrust into the hypodermal tissue 37 while carrying the root portion 31, as shown in FIG. 17. This thrust of the root portion 31 is continued until it reaches the hypodermal tissue 37 which is located 4 to 7 mm beneath the epidermis 36. This distance or stroke is automatically determined by presetting the length of the key way 5. Although the needle 1 is as thin as 0.2 to 0.25 mm, as has been described before, it is reinforced by its sheath 2 so that it can be prevented from warping.

After the root portion 31 has reached the present position, the needle 1 is gently extracted, as shown in FIG. 18, thus completing the hair implanting operation.

If the hair implanting operation is performed with the use of the hair implanting appliance according to the present invention, the thickness of the needle is so small that the breakage in the epidermis or the hypodermal tissue due to the hair implantation is minimized with the satisfactory result that the fixation percentage of the implanted hairs is high.

It will be obvious to those skilled in the art that various changes may be made without departing from the scope of the invention and the invention is not to be considered limited to what is shown in the drawings and described in the specification.

What is claimed is:

1. A hair implanting appliance comprising:
   means to penetrate the scalp comprising a needle having its leading end formed with a protrusion and a notch of generally U-shape along the side of the leading end of said needle, said notch being sized and shaped to retain the root of an artificial hair to be implanted;
   means to guide said needle without penetrating the scalp comprising a sheath formed with a through hole which has substantially the same inside diameter as the outside diameter of said needle, said sheath having a scalp abutting generally flat leading end and an inclined guide surface extending rearwardly from said scalp abutting generally flat end, said needle being slidably received in said sheath
   (i) such that the leading end of said needle can protrude from said scalp abutting generally flat leading end of said sheath and project into a human skin to a depth necessary for the hair implantation and
   (ii) such that scalp abutting generally flat leading end of said sheath cooperates with said needle to retain the hair root and control the positioning of the hair root in said appliance; and
   means to reciprocate said needle axially to cause the leading end of said needle to protrude from the leading end of said sheath.

2. A hair implanting appliance according to claim 1 wherein the tip of said needle is pointed and the leading end of said sheath has a blunt portion and a diagonally cut portion extending rearwardly and outwardly.

3. A hair implanting appliance comprising:
   means to penetrate the scalp comprising a needle having a protrusion at its leading end with a generally U-shaped notch, said notch being sized and shaped to retain the root of an artificial hair to be implanted.
   means to guide said needle without penetrating the scalp comprising a sheath formed with a through hole which has substantially the same inside diameter as the outside diameter of said needle, said sheath having a scalp abutting leading end and an inclined guide surface extending rearwardly from said scalp abutting end, said needle being slidably received in said sheath
   (i) such that the leading end of said needle can protrude from said scalp abutting leading end of said sheath and project into human skin to a depth necessary for the hair implantation and
   (ii) such that a guide surface comprising a surface of said scalp abutting leading end of said sheath merges with and forms a continuation of a surface of said U-shaped notch, whereby said guide surface of said sheath and said surface of said U-shaped notch of said needle form an enlarged guide portion for the hair root to be retained by said appliance and cooperate to control the positioning of the hair root in said appliance; and means to reciprocate said needle axially to cause the leading end of said needle to protrude from the leading end of said sheath.

4. A hair implanting appliance as set forth in claim 1 or 2 wherein the leading end of said sheath is obliquely cut.

5. A hair implanting appliance as set forth in claim 1 or claim 3 wherein the leading open end of said sheath has one semicircumference cut at an angle inclined rearwardly.

6. A hair implanting appliance is set forth in claim 1 or claim 3 further comprising means to prevent rotation of said needle in the circumferential direction with respect to said sheath.

7. A hair implanting appliance is set forth in claim 1 or claim 3, wherein said needle has an exterior diameter of about 0.2–0.25 mm.

8. A hair implanting appliance is set forth in claim 1 or claim 3, wherein said needle is spring biased to a retracted position within said sheath.

9. A hair implanting appliance as set forth in claim 1 or claim 3, wherein said means to reciprocate said needle comprises a handle member connected to said needle and extending from the opposite end of said sheath, said handle having a head portion spaced from the end of said sheath, when said needle is retracted, a distance equal to the depth of proportion of said needle from the sheath and into the skin.

10. A hair implanting appliance according to claim 3, wherein said guide surface of said sheath consists of said surface of scalp abutting leading end.

11. A hair implanting appliance according to claim 3, wherein said guide surface of said sheath consists of said surface of scalp abutting leading end and a part of said inclined surface.

12. A hair implanting appliance according to claim 11, wherein the angle of inclination of said inclined surface of said sheath is the same as the angle of inclination of said inclined surface of said U-shaped notch.

* * * * *